US009408568B2

(12) United States Patent
Fletcher et al.

(10) Patent No.: US 9,408,568 B2
(45) Date of Patent: Aug. 9, 2016

(54) BIOLOGICAL FLUID SAMPLING DEVICE

(71) Applicant: Becton, Dickinson and Company, Franklin Lakes, NJ (US)

(72) Inventors: Gary D. Fletcher, Sparta, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 155 days.

(21) Appl. No.: 14/251,727

(22) Filed: Apr. 14, 2014

(65) Prior Publication Data

US 2014/0309558 A1    Oct. 16, 2014

Related U.S. Application Data

(60) Provisional application No. 61/811,918, filed on Apr. 15, 2013.

(51) Int. Cl.
*A61B 5/00* (2006.01)
*A61B 5/15* (2006.01)
(Continued)

(52) U.S. Cl.
CPC ......... *A61B 5/150213* (2013.01); *A61B 5/1411* (2013.01); *A61B 5/151* (2013.01);
(Continued)

(58) Field of Classification Search
CPC ........... A61B 5/1411; A61B 5/150231; A61B 5/150305; A61B 5/150343; A61B 5/150755; A61J 1/2096; B01L 3/502753; G01N 1/405; G01N 33/491; G01N 1/28; A61M 1/34
USPC ................... 600/573, 576; 604/190, 256, 905; 604/164.11; 210/335, 257.2, 321.62, 210/321.65; 530/390.5, 414, 417, 427; 251/149.1, 149.6; 422/44
See application file for complete search history.

(56) References Cited

U.S. PATENT DOCUMENTS

| 3,322,114 A | 5/1967 | Portnoy et al. |
| 3,640,393 A | 2/1972 | Hurtig |

(Continued)

FOREIGN PATENT DOCUMENTS

| CN | 1262606 A | 8/2000 |
| CN | 1382966 A | 12/2002 |

(Continued)

OTHER PUBLICATIONS

Membrane Separation Technology for Research and Quality Control, Sartorius AG, Separation Technology, Laboratory Filtration; Mar. 1, 1997.

*Primary Examiner* — Max Hindenburg
(74) *Attorney, Agent, or Firm* — The Webb Law Firm (57) ABSTRACT

A biological fluid sampling device adapted to receive a blood sample and includes a housing having a reservoir disposed therein and a first cavity in fluid communication with the reservoir is disclosed. The biological fluid sampling device includes a first test element removably receivable within the first cavity and a lancet having a puncturing element. Additionally, the housing may include a second cavity in fluid communication with the reservoir and a second test element removably receivable within the second cavity. With the blood sample received within the reservoir of the biological fluid sampling device, the first test element and the second test element are adapted to receive a portion of the blood sample. In this manner, the biological fluid sampling device allows for a blood sample to be collected on a plurality of test elements simultaneously. In one embodiment, the biological fluid sampling device contains a sample stabilizer.

21 Claims, 8 Drawing Sheets

(51) Int. Cl.

| | | |
|---|---|---|
| *G01N 33/49* | (2006.01) | |
| *A61M 1/34* | (2006.01) | |
| *G01N 1/28* | (2006.01) | |
| *G01N 1/40* | (2006.01) | |
| *G01N 1/34* | (2006.01) | |
| *B01L 3/00* | (2006.01) | |
| *B04B 7/08* | (2006.01) | |
| *A61B 5/151* | (2006.01) | |
| *A61B 5/157* | (2006.01) | |

(52) U.S. Cl.
CPC .......... *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A | | 4/1985 | Nielsen et al. |
| 4,627,445 A | | 12/1986 | Garcia et al. |
| 5,055,203 A | | 10/1991 | Columbus |
| 5,163,442 A | | 11/1992 | Ono |
| 5,219,999 A | * | 6/1993 | Suzuki .................. C07K 16/065 530/390.5 |
| 5,422,018 A | | 6/1995 | Saunders et al. |
| 5,636,640 A | | 6/1997 | Staehlin |
| 5,726,026 A | | 3/1998 | Wilding et al. |
| 5,839,715 A | | 11/1998 | Leinsing |
| 5,922,591 A | | 7/1999 | Anderson et al. |
| 6,063,039 A | | 5/2000 | Cunningham et al. |
| 6,074,183 A | | 6/2000 | Allen et al. |
| 6,264,619 B1 | | 7/2001 | Ferguson |
| 6,506,167 B1 | | 1/2003 | Ishimito et al. |
| 6,869,405 B2 | | 3/2005 | Marsden |
| 7,803,123 B2 | | 9/2010 | Perez et al. |
| 8,158,410 B2 | | 4/2012 | Tang et al. |
| 8,328,735 B2 | | 12/2012 | Haar et al. |
| 2002/0009015 A1 | | 1/2002 | Laugharn, Jr. et al. |
| 2002/0143298 A1 | * | 10/2002 | Marsden ................ G01N 1/405 604/190 |
| 2003/0134416 A1 | | 7/2003 | Yamanishi et al. |
| 2004/0142463 A1 | | 7/2004 | Walker et al. |
| 2004/0143226 A1 | | 7/2004 | Marsden |
| 2004/0230216 A1 | | 11/2004 | Levaughn et al. |
| 2005/0015020 A1 | | 1/2005 | LeVaughn et al. |
| 2005/0069459 A1 | | 3/2005 | Ahn et al. |
| 2005/0214927 A1 | | 9/2005 | Haley |
| 2006/0029923 A1 | | 2/2006 | Togawa et al. |
| 2006/0240964 A1 | | 10/2006 | Lolachi et al. |
| 2007/0031283 A1 | | 2/2007 | Davis et al. |
| 2007/0160503 A1 | | 7/2007 | Sethu et al. |
| 2008/0135502 A1 | | 6/2008 | Pyo et al. |
| 2008/0240990 A1 | | 10/2008 | Flaherty |
| 2009/0004060 A1 | | 1/2009 | Omuro et al. |
| 2009/0136982 A1 | | 5/2009 | Tang et al. |
| 2009/0181411 A1 | | 7/2009 | Battrell et al. |
| 2009/0204026 A1 | | 8/2009 | Crawford et al. |
| 2010/0089815 A1 | | 4/2010 | Zhang et al. |
| 2010/0093551 A1 | | 4/2010 | Montagu |
| 2010/0198108 A1 | | 8/2010 | Alden |
| 2010/0241031 A1 | | 9/2010 | Lai |
| 2011/0124130 A1 | | 5/2011 | Wagner et al. |
| 2011/0124984 A1 | | 5/2011 | Rostaing |
| 2012/0152858 A1 | | 6/2012 | Yang |
| 2012/0275955 A1 | * | 11/2012 | Haghgooie .......... A61B 5/1411 422/44 |
| 2012/0277696 A1 | | 11/2012 | Gonzalez-Zugasti et al. |
| 2012/0277697 A1 | | 11/2012 | Haghgooie et al. |
| 2013/0026085 A1 | | 1/2013 | Samsoondar |
| 2013/0052675 A1 | | 2/2013 | Karlsson et al. |
| 2013/0082012 A1 | | 4/2013 | Lean et al. |
| 2013/0086980 A1 | | 4/2013 | Gadini et al. |
| 2013/0175213 A1 | | 7/2013 | Dorrer et al. |
| 2013/0209331 A1 | | 8/2013 | Rodenfels et al. |

FOREIGN PATENT DOCUMENTS

| | | |
|---|---|---|
| CN | 1525834 A | 9/2004 |
| CN | 1929782 A | 3/2007 |
| CN | 101102847 A | 1/2008 |
| CN | 101288592 A | 10/2008 |
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 2004361419 A | 12/2004 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

BIOLOGICAL FLUID SAMPLING DEVICE

CROSS-REFERENCE TO RELATED APPLICATION

The present application claims priority to U.S. Provisional Application No. 61/811,918, filed Apr. 15, 2013, entitled "Medical Device for Collection of a Biological Sample", the entire disclosure of which is hereby incorporated by reference.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid sampling device adapted to receive a blood sample and includes a housing having a reservoir disposed therein and a first cavity in fluid communication with the reservoir. The biological fluid sampling device of the present disclosure incorporates the concepts of lancing, blood collection, and multiple test strip collection. The biological fluid sampling device includes a first test element removably receivable within the first cavity and a lancet having a puncturing element. Additionally, the housing may include a second cavity in fluid communication with the reservoir and a second test element removably receivable within the second cavity. With the blood sample received within the reservoir of the biological fluid sampling device, the first test element and the second test element are adapted to receive a portion of the blood sample. In this manner, the biological fluid sampling device allows for a blood sample to be collected on a plurality of test elements simultaneously. For example, the biological fluid sampling device allows for only a single stick on a patient and collection of a blood sample into multiple test strips for a point-of-care testing device. In one embodiment, a portion of the biological fluid sampling device contains a sample stabilizer to promote efficient mixing with the blood sample. The sample stabilizer can be an anticoagulant, or a substance designed to preserve a specific element within the blood such as, for example, RNA, protein analyte, or other element.

In accordance with an embodiment of the present invention, a biological fluid sampling device includes a housing having an inlet port, a reservoir disposed within the housing and in fluid communication with the inlet port, and a first cavity in fluid communication with the reservoir. The device also includes a first test element removably receivable within the first cavity, and a puncturing element, a portion of which is disposed within the housing and adapted for movement between a pre-actuated position wherein the puncturing element is retained within the housing, and a puncturing position wherein the puncturing element extends through the inlet port of the housing.

In certain configurations, the biological fluid sampling device is adapted to receive a blood sample. The housing may include an upper portion and a lower portion, with the inlet port provided within the lower portion. The device may also include an adhesive disposed on a bottom surface of the lower portion. The reservoir may be adapted to receive the blood sample via the inlet port. The upper portion may be a resiliently deformable member and the upper portion may be transitionable between an undeformed position and a deformed position. Actuation of the upper portion from the undeformed position to the deformed position may move the puncturing element from the pre-actuated position to the puncturing position. After the puncturing element moves to the puncturing position, the upper portion returns to its undeformed position and returns the puncturing element to the pre-actuated position. When the blood sample is received within the reservoir, the first test element is adapted to receive a portion of the blood sample.

In additional configurations, the housing also includes a second cavity in fluid communication with the reservoir. A second test element may be removably receivable within the second cavity. The device may also include a check valve in the upper portion. Optionally, a first portion of the housing may include a first sample stabilizer. A second portion of the housing may also include a second sample stabilizer.

In accordance with another embodiment of the present invention, a biological fluid sampling device includes a housing having an inlet port, a reservoir disposed within the housing and in fluid communication with the inlet port, a first cavity in fluid communication with the reservoir, and a second cavity in fluid communication with the reservoir. The device also includes a first test element removably receivable within the first cavity, a second test element removably receivable within the second cavity, and a puncturing element. A portion of the puncturing element is disposed within the housing and adapted for movement between a pre-actuated position, wherein the puncturing element is retained within the housing and a puncturing position wherein the puncturing element extends through the inlet port of the housing.

In accordance with yet another embodiment of the present invention, a biological fluid sampling device adapted to receive a blood sample includes a housing having a resiliently deformable upper portion, a lower portion, and an inlet port within the lower portion. The device also includes a reservoir disposed within the housing and in fluid communication with the inlet port. The reservoir is adapted to receive the blood sample via the inlet port. The device also includes a first cavity in fluid communication with the reservoir. The upper portion of the housing is transitionable between an undeformed position and a deformed position. The device also includes a first test element removably receivable within the first cavity, and a puncturing element, a portion of which is disposed within the housing and adapted for movement between a pre-actuated position wherein the puncturing element is retained within the housing and a puncturing position wherein the puncturing element extends through the inlet port of the housing. Actuation of the upper portion from the undeformed position to the deformed position moves the puncturing element from the pre-actuated position to the puncturing position. After the puncturing element moves to the puncturing position, the upper portion returns to its undeformed position and returns the puncturing element to the pre-actuated position. When the blood sample is received within the reservoir, the first test element is adapted to receive a portion of the blood sample.

In certain configurations, the device includes an adhesive disposed on an outside surface of the lower portion. The housing may also include a second cavity in fluid communication with the reservoir, and a second test element may be removably receivable within the second cavity. When the blood sample is received within the reservoir, the first test element may be adapted to receive a first portion of the blood sample and the second test element may be adapted to receive a second portion of the blood sample. The device may also include a check valve in the upper portion.

In accordance with yet another embodiment of the present invention, a biological fluid testing system for a blood sample includes a biological fluid sampling device adapted to receive the blood sample. The biological fluid sampling device includes a housing having a resiliently deformable upper portion, a lower portion, an inlet port at the lower portion, and a reservoir disposed within the housing and in fluid communication with the inlet port. The reservoir is adapted to receive the blood sample via the inlet port. The device also includes a first cavity in fluid communication with the reservoir. The upper portion of the housing is transitionable between an undeformed position and a deformed position. The device also includes a first test element removably receivable within the first cavity, and a puncturing element. A portion of the puncturing element is disposed within the housing and is adapted for movement between a pre-actuated position wherein the puncturing element is retained within the housing and a puncturing position wherein the puncturing element extends through the inlet port of the housing. Actuation of the upper portion from the undeformed position to the deformed position moves the puncturing element from the pre-actuated position to the puncturing position. After the puncturing element moves to the puncturing position, the upper portion returns to its undeformed position and returns the puncturing element to the pre-actuated position. When the blood sample is received within the reservoir, the first test element is adapted to receive a portion of the blood sample. The system also includes a biological fluid testing device adapted to receive the first test element for closed transfer of the blood sample from the first test element to the biological fluid testing device.

In certain configurations, the blood testing device includes a point-of-care testing device. The housing may also include a second cavity in fluid communication with the reservoir, and a second test element may be removably receivable within the second cavity. When the blood sample is received within the reservoir, the first test element may be adapted to receive a portion of the blood sample and the second test element may be adapted to receive a portion of the blood sample.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood at the point of care without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample resulting in improved operator safety and reducing chance of exposure to blood-borne pathogens; 3) improving sample quality by blocking sample contact with a skin surface of a patient or the atmosphere, both of which can cause analytical errors; 4) improving the overall ease of use; 5) separating the sample at the point of collection; and 6) allowing for the introduction of multiple, non-chemically compatible additives or sample stabilizers from a single lancing action.

FIGS. 1-7 illustrate an exemplary embodiment of the present disclosure. The biological fluid sample device, such as a blood sampling device of the present disclosure incorporates the concepts of lancing, blood collection, and multiple test strip collection. Referring to FIGS. 1-7, a biological fluid sampling device, such as a blood sampling device 10 of the present disclosure, is adapted to receive a plurality of test elements 12 and includes a lancet structure 14. The blood sampling device 10 is adapted to receive a blood sample 16 (FIG. 6) and the test elements 12 are adapted to receive a portion of the blood sample 16. In this manner, the blood sampling device 10 of the present disclosure allows for a blood sample to be collected on a plurality of test elements simultaneously. For example, the blood sampling device 10 allows for only a single stick on a patient and collection of a blood sample into multiple test strips for a point-of-care testing device.

FIGS. 1-8 illustrate an exemplary embodiment of the present disclosure. Referring to FIGS. 1-8, a biological fluid testing system, such as a blood testing system 20 of the present disclosure, includes a blood sampling device 10 and a blood testing device or point-of-care testing device 200. The blood sampling device 10 is adapted to receive a plurality of test elements 12 and includes a lancet structure 14. The blood sampling device 10 is adapted to receive a blood sample 16 (FIG. 6) and the test elements 12 are adapted to receive a portion of the blood sample 16. In this manner, the blood sampling device 10 of the present disclosure allows for a blood sample to be collected on a plurality of test elements simultaneously. For example, the blood sampling device 10 allows for only a single stick on a patient and collection of a blood sample into multiple test strips for a point-of-care testing device 200. The blood testing device 200 is adapted to receive a test element 12 to analyze the blood sample and obtain test results.

Figure 3:
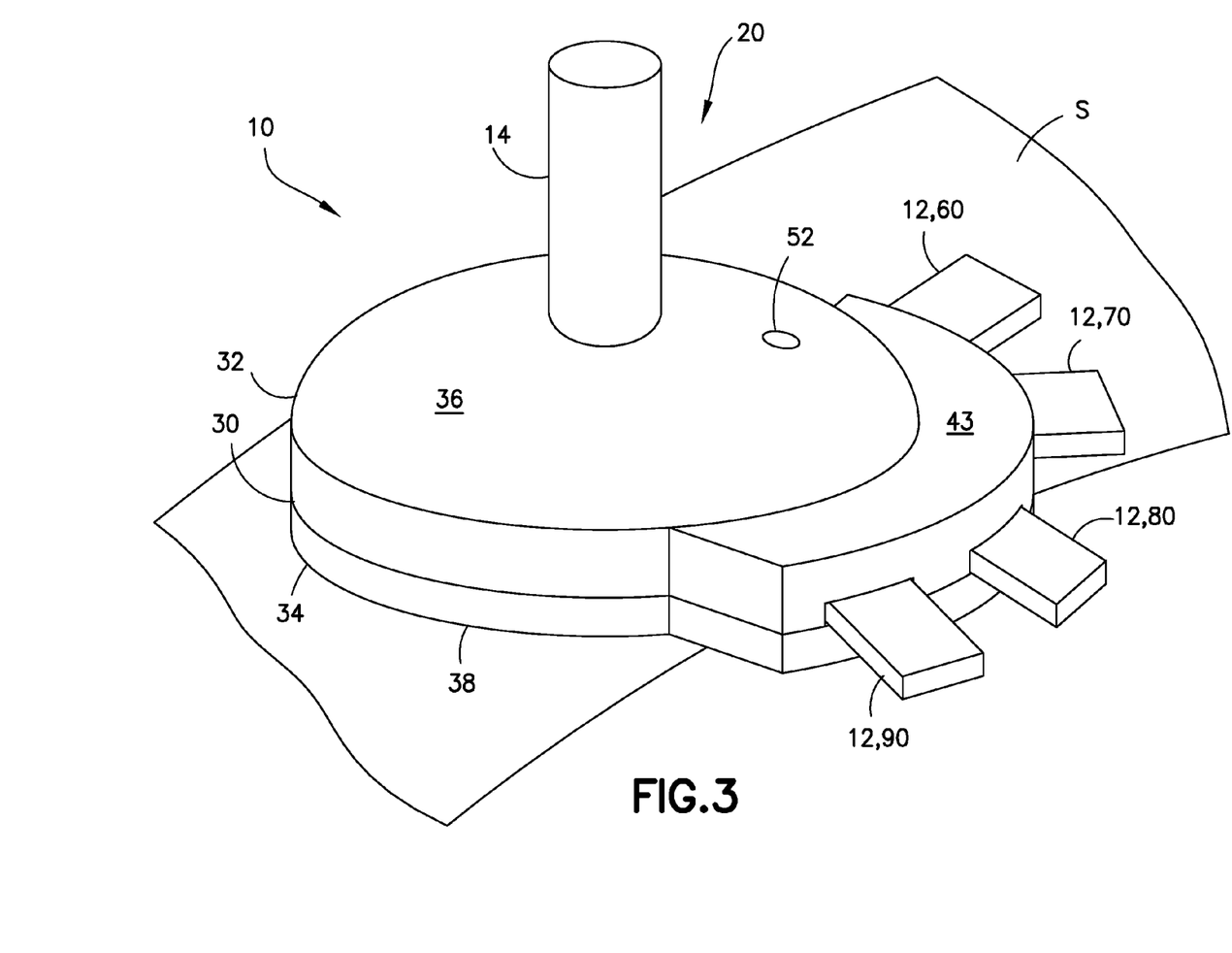
FIG. 3 is a perspective view of a biological fluid sampling device secured to a patient with a housing in an undeformed position in accordance with an embodiment of the present invention.
Figure 4:
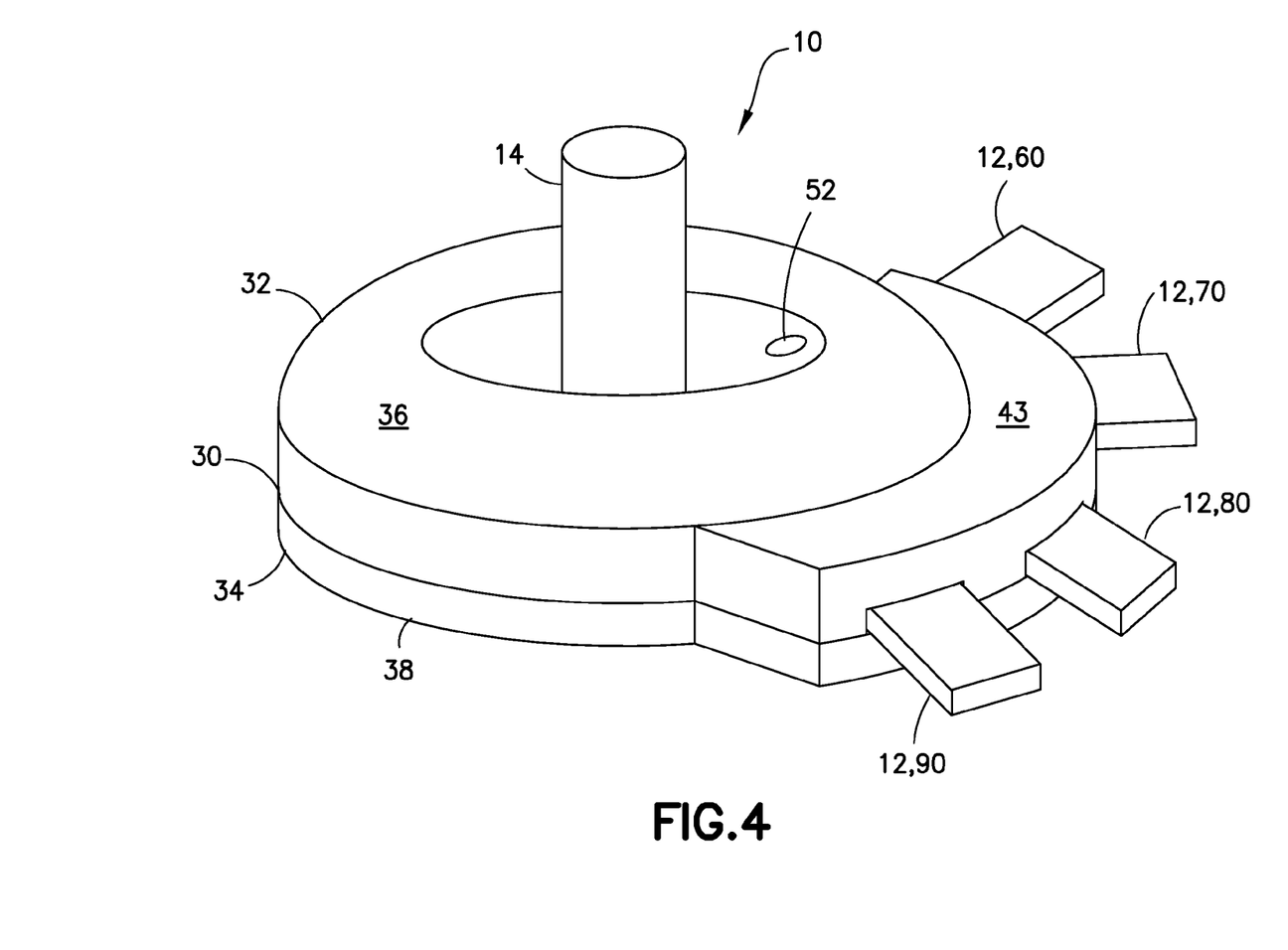
FIG. 4 is a perspective view of a biological fluid sampling device secured to a patient with a housing in a deformed position in accordance with an embodiment of the present invention.
Figure 5:
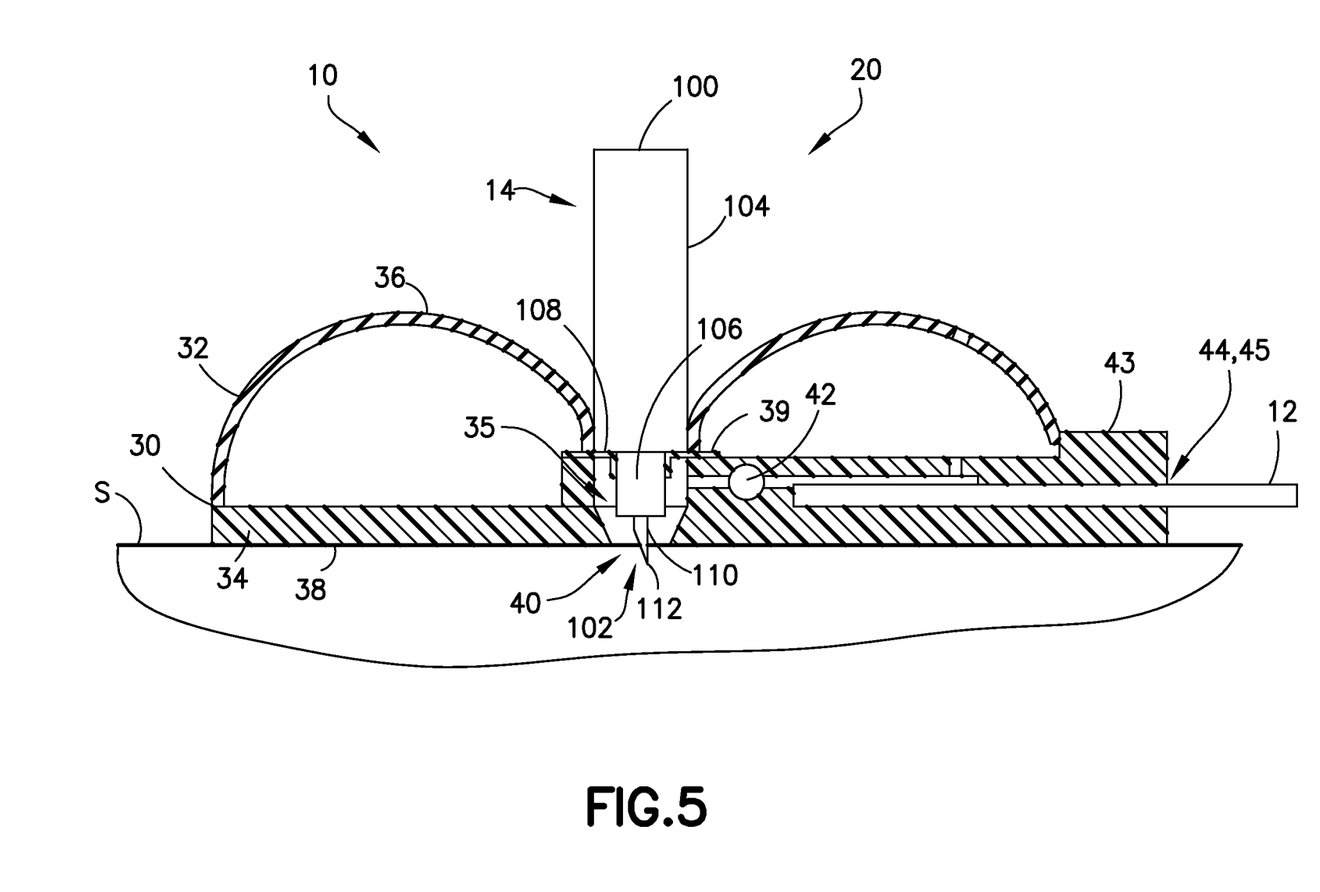
FIG. 5 is a cross-sectional view of the biological fluid sampling device of FIG. 4 in accordance with an embodiment of the present invention.
Figure 6:
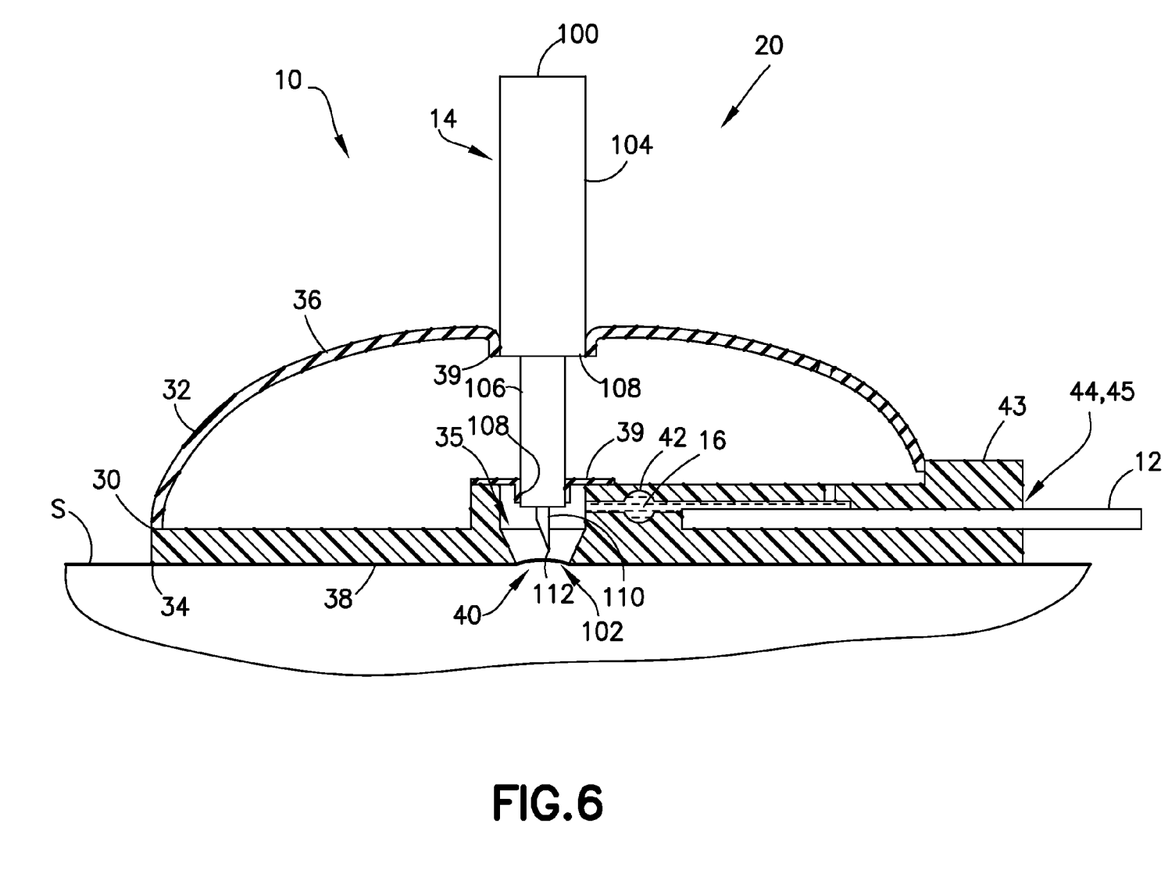
FIG. 6 is a cross-sectional view of the biological fluid sampling device of FIG. 3 with a blood sample received within the biological fluid sampling device in accordance with an embodiment of the present invention.

Referring to FIGS. 1-7, the blood sampling device 10 generally includes a housing 30 having an upper portion 32 and a lower portion 34. The upper portion 32 and the lower portion 34 are secured theretogether such that significant relative movement between the upper portion 32 and the lower portion 34 is prevented. The housing 30 defines a central aperture 35 therethrough the upper portion 32 and the lower portion 34. The lancet structure 14 is positioned within the central aperture 35 as shown in FIGS. 1-6. The housing 30 includes a lancet engagement portion 39 for securing the lancet structure 14 within the central aperture 35 as shown in FIGS. 5 and 6. The housing 30 also includes a docking portion 43 located around a portion of the upper portion 32 and the lower portion 34. The docking portion 43 is secured to the upper portion 32 and the lower portion 34 such that significant relative movement between the docking portion 43 and the upper portion 32 and the lower portion 34 is prevented.

The upper portion 32 includes a dome-shaped surface 36 and the lower portion 34 includes a bottom surface 38. Referring to FIGS. 3, 5, and 6, the bottom surface 38 includes an adhesive so that the blood sampling device 10 can be secured onto a skin surface S of a patient where a blood sample will be accessed. In one embodiment, the adhesive of the bottom surface 38 is protected by a peel-off layer, similar to an adhesive bandage, which would be removed before placing the blood sampling device 10 on the skin surface S of the patient's body. A hydrogel or other layer (not shown) could be included to provide some thickness to the bottom surface 38 of the lower portion 34 and help improve the stability of the adhesive seal. Additionally, in one embodiment, the adhesive could include a chemistry to create a more liquid-tight seal, similar to painter's tape technology, where wetting from the paint itself causes a chemical reaction with the adhesive to create a more water-tight barrier to prevent the paint from seeping under the tape.

The upper portion 32 is a resiliently deformable member that is transitionable between an undeformed position (FIGS. 3 and 6) and a deformed position (FIGS. 4 and 5) as will be discussed in more detail below. The upper portion 32 is formed of a flexible material such that the upper portion 32 can be depressed by pressure applied by a user. After the pressure is removed, the upper portion 32 returns to its original or undeformed position and its domed-shape. In one embodiment, the upper portion 32 of the housing 30 includes a vent or check valve 52 to allow air to be expelled upon depression of the dome-shaped upper portion 32.

Referring to FIGS. 1-7, the housing 30 of the blood sampling device 10 generally includes an inlet port 40 defined through the bottom surface 38 of the lower portion 34 and a reservoir or fluid channel 42 disposed within the housing 30 and in fluid communication with the inlet port 40. The reservoir or fluid channel 42 may have a variety of different shapes and sizes to accommodate a blood sample that can then be dispersed to a plurality of test strips received within respective test strip docks. In this manner, the blood sampling device 10 of the present disclosure allows for a blood sample to be collected on a plurality of test strips simultaneously. For example, the blood sampling device 10 allows for only a single stick on a patient and collection of a blood sample into multiple test strips for a point-of-care testing device as discussed in more detail below.

The housing 30 also includes a first cavity or first test strip dock 44 having a first outlet port 45, a second cavity or second test strip dock 46 having a second outlet port 47, a third cavity or third test strip dock 48 having a third outlet port 49, and a fourth cavity or fourth test strip dock 50 having a fourth outlet port 51. The first test strip dock 44, the second test strip dock 46, the third test strip dock 48, and the fourth test strip dock 50 extend through the docking portion 43 and a portion of the upper portion 32 and the lower portion 34 of the housing 30. In one embodiment, the first test strip dock 44, the second test strip dock 46, the third test strip dock 48, and the fourth test strip dock 50 may extend through the docking portion 43 and between the upper portion 32 and the lower portion 34 of the housing 30. Each of the first test strip dock 44, the second test strip dock 46, the third test strip dock 48, and the fourth test strip dock 50 are in fluid communication with the reservoir or fluid channel 42 disposed within the housing 30.

Although FIGS. 1-7 illustrate the housing 30 of the blood sampling device 10 having four test strip docks, it is envisioned that the housing 30 can contain any number of test strip docks. For example, in one embodiment, the housing 30 of the blood sampling device 10 may include more than four test strip docks that can each receive a test element therein.

Figure 1:
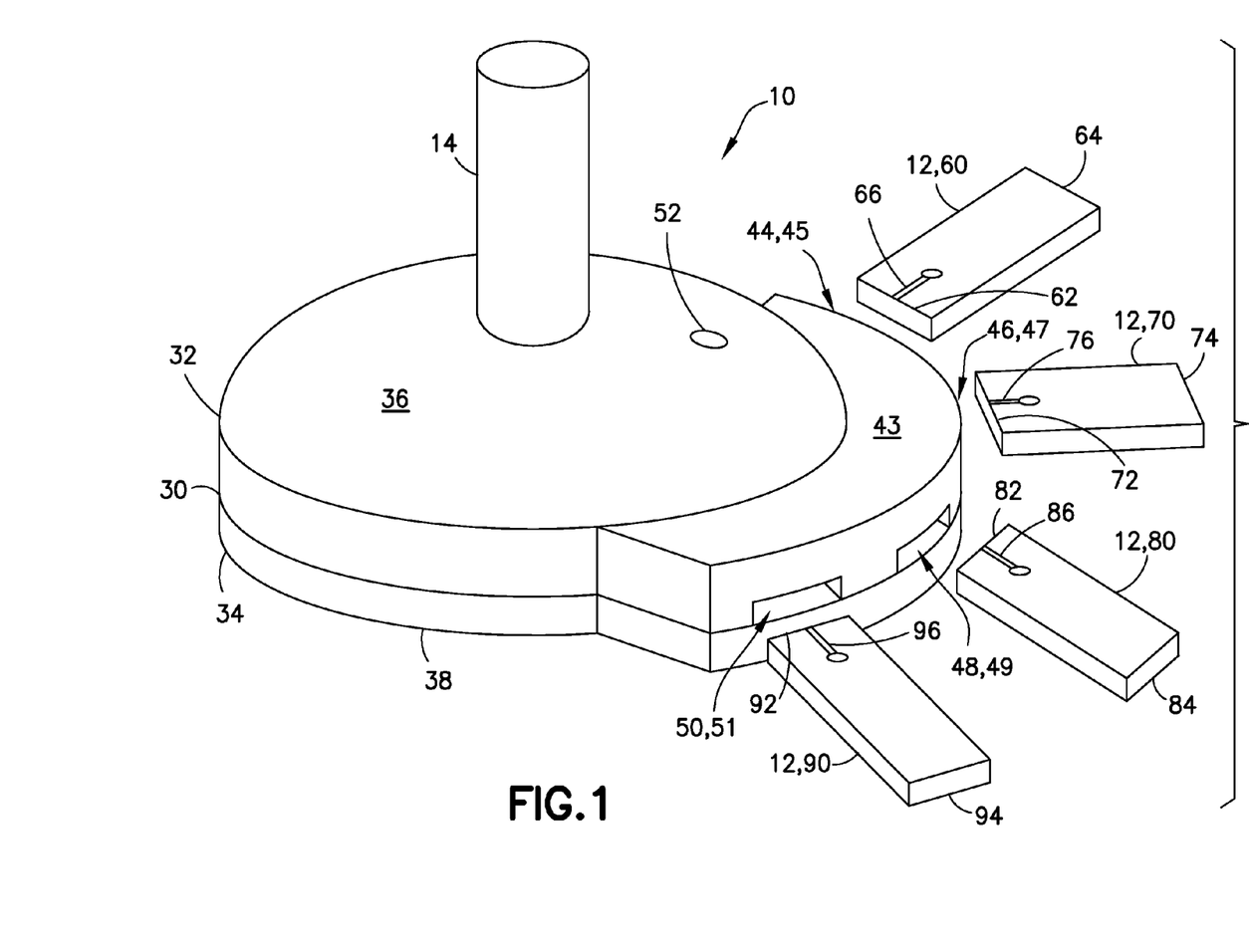
FIG. 1 is an exploded, perspective view of a biological fluid sampling device in accordance with an embodiment of the present invention.
Figure 2:
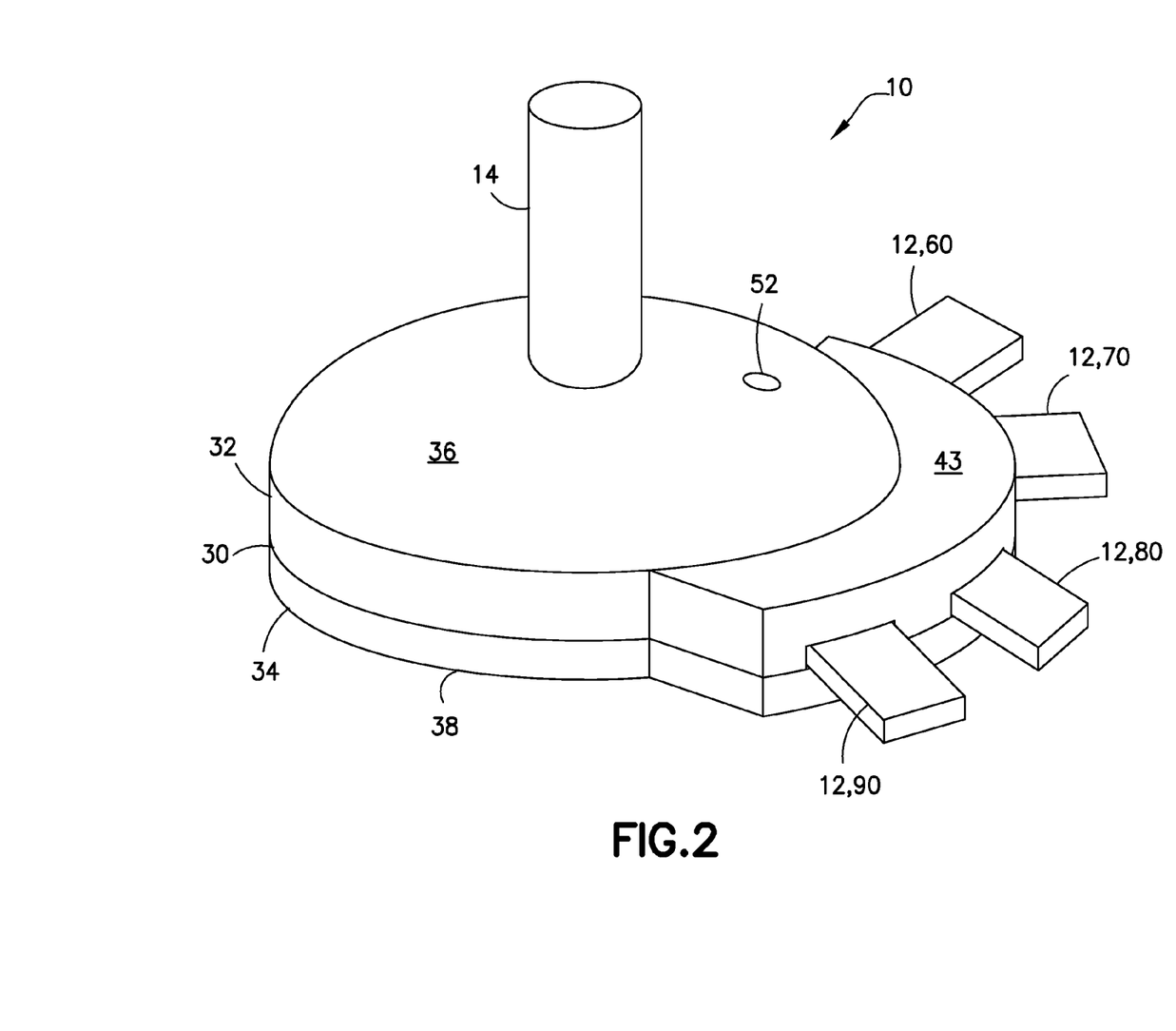
FIG. 2 is an assembled, perspective view of a biological fluid sampling device in accordance with an embodiment of the present invention.

Each of the first test strip dock 44, the second test strip dock 46, the third test strip dock 48, and the fourth test strip dock 50 are sized and adapted to receive a test strip or test element 12 therein. For example, a first test element or first test strip 60 that includes a first end 62, a second end 64, and a blood receiving cavity 66 is removably receivable within the first test strip dock 44 as shown in FIGS. 1 and 2. The blood receiving cavity 66 of the first test element 60 is adapted to receive a portion of a blood sample contained within the reservoir 42 of the housing 30 of the blood sampling device 10. A second test element or second test strip 70 that includes a first end 72, a second end 74, and a blood receiving cavity 76 is removably receivable within the second test strip dock 46 as shown in FIGS. 1 and 2. The blood receiving cavity 76 of the second test element 70 is adapted to receive a portion of a blood sample contained within the reservoir 42 of the housing 30 of the blood sampling device 10. Furthermore, a third test element or third test strip 80 that includes a first end 82, a second end 84, and a blood receiving cavity 86 is removably receivable within the third test strip dock 48 as shown in FIGS. 1 and 2. The blood receiving cavity 86 of the third test element 80 is adapted to receive a portion of a blood sample contained within the reservoir 42 of the housing 30 of the blood sampling device 10. Also, a fourth test element or fourth test strip 90 that includes a first end 92, a second end 94, and a blood receiving cavity 96 is removably receivable within the fourth test strip dock 50 as shown in FIGS. 1 and 2. The blood receiving cavity 96 of the fourth test element 90 is adapted to receive a portion of a blood sample contained within the reservoir 42 of the housing 30 of the blood sampling device 10. Thus, each of the test strip docks are configured to receive a test strip therein and position the test strip in fluid communication with an inner portion of the blood sampling device 10, i.e., the reservoir 42.

Referring to FIGS. 1-6, the blood sampling device 10 also includes a lancet or lancet structure 14 that may be secured within the central aperture 35 of the housing 30. The lancet 14 generally includes a first end 100, a second end 102, a top or handle portion 104 adjacent the first end 100, a bottom or lancet portion 106 adjacent the second end 102, and a housing engagement portion 108. The housing engagement portion 108 engages the lancet engagement portion 39 of the housing for securing the lancet 14 to the housing 30 within central aperture 35 as shown in FIGS. 5 and 6. Referring to FIGS. 5 and 6, a portion of the lancet 14 is disposed within the housing 30 of the blood sampling device 10. The lancet portion 106 includes a puncturing element 110 having a puncturing end 112. The puncturing end 112 is adapted for puncturing the skin surface S of a patient (FIG. 5), and may define a pointed end, a blade edge, or a similar cutting mechanism. The puncturing end 112 may include a preferred alignment orientation, such as with a pointed end of a blade aligned in a specific orientation.

The lancet 14 is adapted for movement between a pre-actuated position (FIGS. 3 and 6) wherein the puncturing element 110 including the puncturing end 112 is retained within the housing 30 and a puncturing position (FIGS. 4 and 5) wherein the puncturing end 112 of the puncturing element 110 extends through the inlet port 40 of the housing 30 to puncture a skin surface S of a patient to draw a blood sample as discussed in more detail below.

In one embodiment, the housing 30 of the blood sampling device 10 may include a self-sealing dock that would allow an external lancet to be removably received within the housing 30. The external lancet could be either pre-integrated into the packaged device or introduced separately by a user before using the blood sampling device 10 of the present disclosure.

Figure 8:
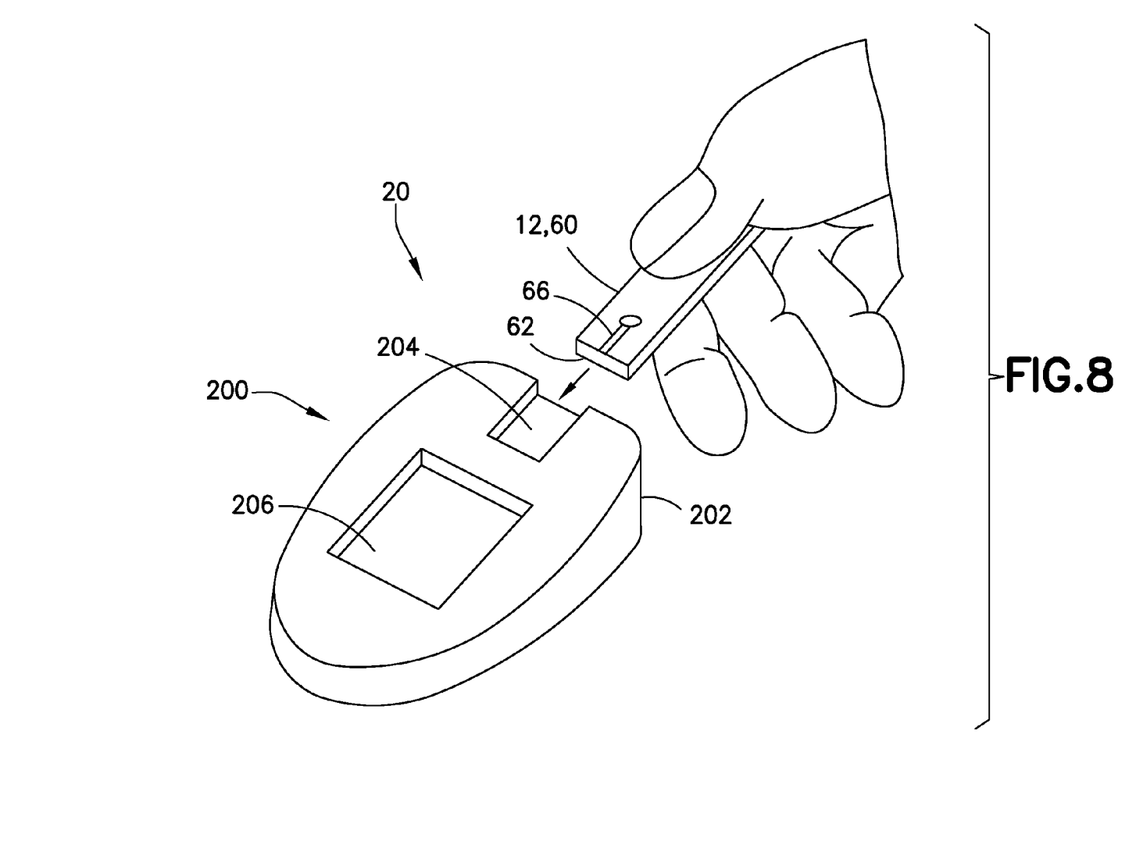
FIG. 8 is a perspective view of a test element and a point-of-care testing device in accordance with an embodiment of the present invention.

Referring to FIG. 8, a blood testing device or point-of-care testing device 200 generally includes a test strip reader 202, a receiving port 204 for receiving a test strip 12, and a viewing window 206. The blood testing device 200 is adapted to receive a test element 12 to analyze the blood sample and obtain test results. The receiving port 204 of the point-of-care testing device 200 allows for the closed transfer of a blood sample from a test element 12 to the point-of-care testing device 200.

Referring to FIGS. 1-8, use of a blood sampling device of the present disclosure will now be described. Initially, each of the test strip docks receive a test strip therein to position each of the test strips in fluid communication with an inner portion of the blood sampling device 10, i.e., the reservoir 42. For example, referring to FIGS. 1 and 2, the first end 62 of the first test strip 60 can be placed within the first outlet port 45 of the first test strip dock 44 until the first test strip 60 is received within the first test strip dock 44. The first end 72 of the second test strip 70 can be placed within the second outlet port 47 of the second test strip dock 46 until the second test strip 70 is received within the second test strip dock 46. Also, the first end 82 of the third test strip 80 can be placed within the third outlet port 49 of the third test strip dock 48 until the third test strip 80 is received within the third test strip dock 48. Furthermore, the first end 92 of the fourth test strip 90 can be placed within the fourth outlet port 51 of the fourth test strip dock 50 until the fourth test strip 90 is received within the fourth test strip dock 50.

Referring to FIG. 3, upon selecting a site, a clinician can adhere the adhesive on the bottom surface 38 of the lower portion 34 of the housing 30 onto a skin surface S of a patient where a blood sample will be accessed over a selected sampling site as shown in FIG. 3.

Referring to FIGS. 3-5, a user or an operator may then apply pressure to the dome-shaped surface 36 of the upper portion 32 of the housing 30 to actuate the upper portion 32 from the undeformed position (FIGS. 3 and 6) to the deformed position (FIGS. 4 and 5). Actuation of the upper portion 32 from the undeformed position (FIGS. 3 and 6) to the deformed position (FIGS. 4 and 5) moves the lancet 14 from the pre-actuation position (FIGS. 3 and 6) to the puncturing position (FIGS. 4 and 5) thereby causing the lancing of the skin surface S of the patient by the puncturing end 112 of the lancet 14 as shown in FIG. 5. When the upper portion 32 of the housing 30 is depressed, the puncturing end 112 of the lancet 14 cuts into the skin surface S of the patient's body and capillary blood begins to flow into the inlet port 40 of the housing 30.

After lancing and release of the pressure for the lancing action, the domed shape of the upper portion 32 begins to relax and returns to its original shape or undeformed position. This return of the upper portion 32 to its undeformed position creates a gentle vacuum during the process that helps to draw out the capillary blood through the inlet port 40 and to the reservoir or fluid channel 42 of the housing 30. With the upper portion 32 of the housing 30 returned to its undeformed position and with the blood sample 16 received within the reservoir 42 as shown in FIG. 6, the blood sample 16 is directed to flow through the reservoir 42 and to the test strip docks such that the test elements 60, 70, 80, 90 each receive a portion of the blood sample 16. In one embodiment, the reservoir or fluid channel 42 may include microfluidic pathways integrated therein to direct the blood sample 16 to the test strips 60, 70, 80, 90 by capillary action. The blood receiving cavities 66, 76, 86, 96 are adapted to receive a portion of the blood sample therein.

Figure 7:
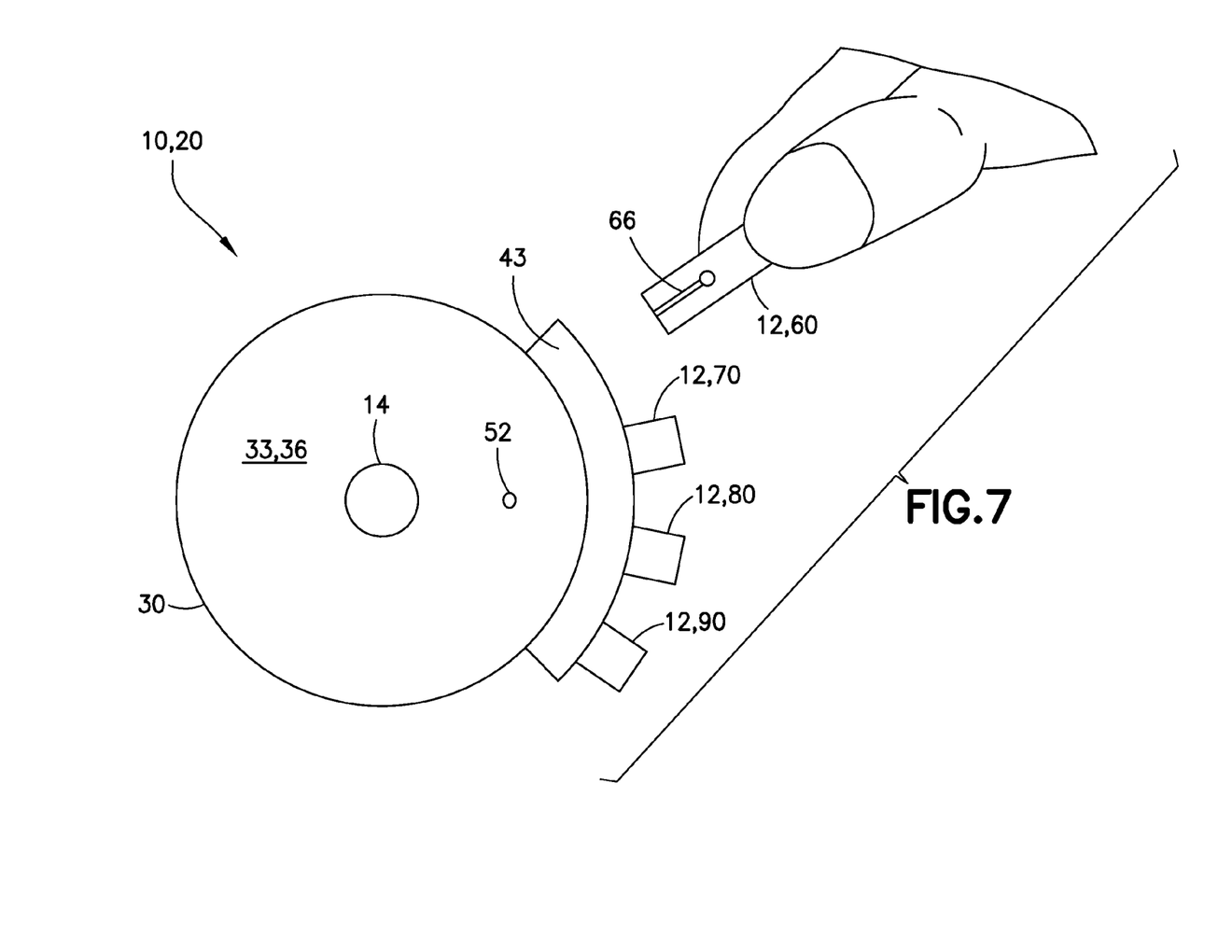
FIG. 7 is a top elevation view of a biological fluid sampling device with a user removing a test element from the biological fluid sampling device in accordance with an embodiment of the present invention.

Referring to FIG. 7, with the blood sample transferred to the test strips or test elements 60, 70, 80, 90, a user or operator may then grasp the second end 64 of the first test strip 60, for example, and pull the first test element 60 from the first test strip dock 44 of the housing 32. Next, referring to FIG. 8, the collected blood sample within the first test strip 60 is transferred to the test strip reader 202 of the point-of-care testing device 200 to analyze the collected blood and obtain test results for tests such as glucose, cholesterol, or other blood sample results. Referring to FIG. 8, the receiving port 204 of the point-of-care testing device 200 allows for the closed transfer of a blood sample from the first test element 60 to the point-of-care testing device 200. In one embodiment, the viewing window 206 of the test strip reader 202 may indicate to an operator desired information. For example, the viewing window 206 may indicate what the point-of-care testing device 200 is analyzing the blood sample for.

In one embodiment, a portion of the blood sampling device 10 contains a sample stabilizer to promote efficient mixing with the blood sample. The sample stabilizer, can be an anticoagulant, or a substance designed to preserve a specific element within the blood such as, for example, RNA, protein analyte, or other element. In one embodiment, the sample stabilizer is provided within the inlet port 40 of the housing 30 of the blood sampling device 10 and/or any area where a primary blood sample is collected. In another embodiment, the sample stabilizer is provided in a portion of any of the reservoirs or fluid channels 42 of the housing 30 of the blood sampling device 10 and/or along any portion of a liquid path that the blood sample travels. In other embodiments, the sample stabilizer may be provided in any of the test strip docks of the blood sampling device 10. In one embodiment, each of the fluid channels, reservoirs, test strip docks, and/or each of the test elements could each include a different sample stabilizer. In this manner, a single blood sample could be used for a variety of different tests, each of which could introduce an appropriate, and potentially unique, sample stabilizer for a desired use. A blood sampling device of the present disclosure provides flexibility in the nature of the additives and/or sample stabilizers introduced for a blood sample.

Referring to FIG. 5, upon actuation of the lancet 14 to puncture the skin surface S, no or minimal blood will seep between the stick site and the housing 30 of the blood sampling device 10, and, importantly, any seeped blood will not subsequently enter the blood sampling device 10.

Collection using the blood sampling device 10 of the present disclosure allows "closed system" capillary blood collection with the following advantages, such as avoiding exposure of the operator or patient to the blood and avoiding exposure of the blood to atmosphere and potentially better preservation of in vivo blood gas concentrations. Also, the blood sampling device 10 of the present disclosure incorporates the concepts of lancing, blood collection, and multiple test strip collection. The blood sampling device 10 of the present disclosure allows for a blood sample to be collected on a plurality of test elements simultaneously. For example, the blood sampling device 10 allows for only a single stick on a patient and collection of a blood sample into multiple test strips for a point-of-care testing device. This ability to collect a single blood sample into multiple test strips reduces the anxiety and discomfort to the patient.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid sampling device, comprising:
    a housing having an inlet port, a reservoir disposed within the housing and in fluid communication with the inlet port, and a first cavity in fluid communication with the reservoir;
    a first test element removably receivable within the first cavity, wherein the first test element is a test strip; and
    a puncturing element, a portion of which is disposed within the housing and adapted for movement between a pre-actuated position wherein the puncturing element is retained within the housing and a puncturing position wherein the puncturing element extends through the inlet port of the housing.

2. The biological fluid sampling device of claim 1, wherein the biological fluid sampling device is adapted to receive a blood sample.

3. The biological fluid sampling device of claim 2, wherein the housing includes an upper portion and a lower portion, the inlet port provided within the lower portion.

4. The biological fluid sampling device of claim 3, further comprising an adhesive disposed on a bottom surface of the lower portion.

5. The biological fluid sampling device of claim 3, wherein the reservoir is adapted to receive the blood sample via the inlet port.

6. The biological fluid sampling device of claim 3, wherein the upper portion is a resiliently deformable member and the upper portion is transitionable between an undeformed position and a deformed position.

7. The biological fluid sampling device of claim 6, wherein the puncturing element is configured to move from the pre-actuated position to the puncturing position upon actuation of the upper portion from the undeformed position to the deformed position,
wherein after the puncturing element moves to the puncturing position, the upper portion is configured to return to its undeformed position and returns the puncturing element to the pre-actuated position, and
wherein with the blood sample received within the reservoir, the first test element is adapted to receive a portion of the blood sample.

8. The biological fluid sampling device of claim 1, wherein the housing further comprises a second cavity in fluid communication with the reservoir, and wherein a second test element is removably receivable within the second cavity.

9. The biological fluid sampling device of claim 3, further comprising a check valve in the upper portion.

10. The biological fluid sampling device of claim 1, wherein a first portion of the housing includes a first sample stabilizer.

11. The biological fluid sampling device of claim 10, wherein a second portion of the housing includes a second sample stabilizer.

12. A biological fluid sampling device, comprising:
a housing having an inlet port, a reservoir disposed within the housing and in fluid communication with the inlet port, a first cavity in fluid communication with the reservoir, and a second cavity in fluid communication with the reservoir;
a first test element removably receivable within the first cavity;
a second test element removably receivable within the second cavity; and
a puncturing element, a portion of which is disposed within the housing and adapted for movement between a pre-actuated position wherein the puncturing element is retained within the , housing and a puncturing position wherein the puncturing element extends through the inlet port of the housing.

13. A biological fluid sampling device adapted to receive a blood sample, the biological fluid sampling device comprising:
a housing having a resiliently deformable upper portion, a lower portion, an inlet port within the lower portion, a reservoir disposed within the housing and in fluid communication with the inlet port, the reservoir adapted to receive the blood sample via the inlet port, and a first cavity in fluid communication with the reservoir, the upper portion transitionable between an undeformed position and a deformed position;
a first test element removably receivable within the first cavity; and
a puncturing element, a portion of which is disposed within the housing and adapted for movement between a pre-actuated position wherein the puncturing element is retained within the housing and a puncturing position wherein the puncturing element extends through the inlet port of the housing,
wherein the puncturing element is configured to move from the pre-actuated position to the puncturing position upon actuation of the upper portion from the undeformed position to the deformed position,
wherein after the puncturing element moves to the puncturing position, the upper portion is configured to return to its undeformed position and returns the puncturing element to the pre-actuated position, and
wherein with the blood sample received within the reservoir, the first test element is adapted to receive a portion of the blood sample.

14. The biological fluid sampling device of claim 13, further comprising an adhesive disposed on an outside surface of the lower portion.

15. The biological fluid sampling device of claim 13, wherein the housing further comprises a second cavity in fluid communication with the reservoir, and wherein a second test element is removably receivable within the second cavity.

16. The biological fluid sampling device of claim 15, wherein with the blood sample received within the reservoir, the first test element is adapted to receive a first portion of the blood sample and the second test element is adapted to receive a second portion of the blood sample.

17. The biological fluid sampling device of claim 13, further comprising a check valve in the upper portion.

18. A biological fluid testing system for a blood sample, the biological fluid testing system comprising:
a biological fluid sampling device adapted to receive the blood sample, the biological fluid sampling device comprising:
a housing having a resiliently deformable upper portion, a lower portion, an inlet port at the lower portion, a reservoir disposed within the housing and in fluid communication with the inlet port, the reservoir adapted to receive the blood sample via the inlet port, and a first cavity in fluid communication with the reservoir, the upper portion transitionable between an undeformed position and a deformed position;
a first test element removably receivable within the first cavity; and
a puncturing element, a portion of which is disposed within the housing and adapted for movement between a pre-actuated position wherein the puncturing element is retained within the housing and a puncturing position wherein the puncturing element extends through the inlet port of the housing,
wherein the puncturing element is configured to move from the re-actuated position to the puncturing position upon actuation of the upper portion from the undeformed position to the deformed position,
wherein after the puncturing element moves to the puncturing position, the upper portion is configured to return to its undeformed position and returns the puncturing element to the pre-actuated position, and
wherein with the blood sample received within the reservoir, the first test element is adapted to receive a portion of the blood sample; and
a blood testing device adapted to receive the first test element for closed transfer of the blood sample from the first test element to the blood testing device.

19. The biological fluid testing system of claim 18, wherein the blood testing device comprises a point-of-care testing device.

20. The biological fluid testing system of claim 18, wherein the housing further comprises a second cavity in fluid communication with the reservoir, and wherein a second test element is removably receivable within the second cavity.

21. The biological fluid testing system of claim 20, wherein with the blood sample received within the reservoir, the first test element is adapted to receive a portion of the blood sample and the second test element is adapted to receive a portion of the blood sample.

\* \* \* \* \*